United States Patent
Bachmann et al.

(10) Patent No.: US 6,386,874 B2
(45) Date of Patent: May 14, 2002

(54) HYGIENE INSTRUMENT FOR CLEANING AND POLISHING THE SURFACE OF THE TEETH AND THE COMPOSITE MATERIALS OF DENTAL FILINGS, IN THE SHAPE OF A ROD

(76) Inventors: Marc William Bachmann; Sonia Bachmann; Noemie Bachmann, all of 20 rue Biron, 34190 Ganges (FR)

( * ) Notice: Subject to any disclaimer, the term of this patent is extended or adjusted under 35 U.S.C. 154(b) by 0 days.

(21) Appl. No.: 09/761,200

(22) Filed: Jan. 16, 2001

Related U.S. Application Data

(63) Continuation-in-part of application No. 09/561,803, filed on May 1, 2000, now abandoned.

(30) Foreign Application Priority Data

Nov. 26, 1999  (EP) .............................. 99440327

(51) Int. Cl.⁷ .............................................. A61C 3/06
(52) U.S. Cl. ..................................................... 433/142
(58) Field of Search ................................. 433/141, 142, 433/146, 147, 125, 166

(56) References Cited

U.S. PATENT DOCUMENTS

| | | | |
|---|---|---|---|
| 2,122,920 A | * 7/1938 | Russell | 433/142 |
| 3,698,388 A | 10/1972 | Muhler | |
| 3,775,848 A | 12/1973 | Barnett | |
| 4,462,136 A | 7/1984 | Nakao et al. | |
| 5,114,438 A | * 5/1992 | Leatherman et al. | 51/296 |
| 5,118,291 A | * 6/1992 | Varaine | 433/142 |
| 5,290,170 A | * 3/1994 | Weissenfluh et al. | 433/142 |
| 5,697,390 A | * 12/1997 | Garrison et al. | 132/321 |
| 5,797,748 A | * 8/1998 | Reynaud et al. | 433/224 |

FOREIGN PATENT DOCUMENTS

| | | |
|---|---|---|
| EP | 0 425 357 A2 | 5/1991 |
| EP | 11192246 | 7/1999 |

* cited by examiner

*Primary Examiner*—Nicholas D. Lucchesi
(74) *Attorney, Agent, or Firm*—Young & Basile, P.C.

(57) ABSTRACT

Hygiene instrument for cleaning and polishing the surface of the teeth and the composite materials of dental fillings, in the shape of a rod.

The structure of the rod is made up of fibers and optionally a load of particles embedded in a resinous matrix giving the working surface of the rod a continuous abrasive power.

11 Claims, 1 Drawing Sheet

Pl.unique

US 6,386,874 B2

HYGIENE INSTRUMENT FOR CLEANING AND POLISHING THE SURFACE OF THE TEETH AND THE COMPOSITE MATERIALS OF DENTAL FILINGS, IN THE SHAPE OF A ROD

This application is a Continuation-In-Part of application Ser. No. 09/561,803 filed on May 1, 2000, now abandoned.

BACKGROUND OF THE INVENTION

The subject of this invention is a hygiene instrument, also called hereinafter polisher, for cleaning and polishing the surface of the teeth and/or the composite materials of dental fillings, the instrument or polisher being designed to be used by private individuals as well as by practitioners of dental art.

One knows that correct maintenance of the teeth consists of daily elimination of dental plaque and food debris from the surface of the teeth and from the spaces between the teeth by careful brushing, followed by the use of instruments used only once, such as toothpicks made of wood, plastic, or bird feathers; single tufted brushes; bottle brushes or dental floss.

However these instruments are not satisfactory.

The sticks, commonly called toothpicks, are made of wood or bird feathers and are not hygienic, they break easily, and they are traumatic to the gums; if made of plastic they are simultaneously too thick and too flexible and don't easily pass between the teeth.

Dental floss, made of silk or nylon materials, is efficient but has problems in crossing the point of contact of the teeth if these latter are too close from each other, and it shreds and remains stuck between the teeth, provoking immediate discomfort. The small brushes and the bottle brushes cannot be used when the spaces between the teeth are narrow, and their high cost is an obstacle to their regular use.

Dental professionals, dentists and hygienists must eliminate deposits, stains, and discolorations of the tooth surface and have, for the cleaning and polishing of the teeth and fillings made of composite materials, a vast array of instruments and devices, such as rotating brushes, instruments to remove tartar, ultrasonic instruments, air-polishers, or also abrasive strips or discs.

However, these instruments present the following drawbacks:

The rotating brushes, used with a cleaning powder, possess a very significant abrasive power which leads to excessive abrasion of the raised tooth surfaces.

The instruments made of stainless steel that remove tartar only act at their points of contact with the tooth and are time and attention demanding, which leads to an elevated cost for a well done job.

Ultrasonic instruments have an end that is too large to go into small fractures.

Air polishers, which work like a micro-sandblaster by projecting a powder at a supersonic speed, unpolish the enamel, and consequently require a careful repolishing of the teeth with another otherwise adapted powder because in the absence of such a repolishing the surface of the teeth very quickly retarnishes.

Abrasive strips, made of fabric or plastic covered with an abrasive glue, introduced between the teeth and moved in a backwards and forwards movements are supposed to polish the proximal sides of the teeth, which requires the practician to hold the bands between the two fingers at each end in the oral cavity: this uncomfortable position does not allow one to correctly guide the strip to make it to conform to the shape of the proximal surface of the tooth. In addition, during, this movement, if this extremely fine strip comes into contact with the gums, it can cut them like a razor and furthermore the strip loses its abrasive coat very quickly, which causes it to unglue itself while crossing over the contact point of the teeth if the teeth are sharp and/or very close from each other.

The abrasive disks, mounted on rotary instruments, are disks of a small diameter made of a plastic material covered with an abrasive material which cut the gums and cannot penetrate the space between the teeth.

Finally, in a dental office, the difficulty, during the finishing and polishing of fillings made of a composite material, rests in the creation of a composite-tooth seal without excess while being perfectly polished. There still is a problem of access and of instrumentation more or less imperfectly adapted and not giving total satisfaction.

SUMMARY OF THE INVENTION

The goal of this invention is to remedy the drawbacks of existing instruments by proposing an instrument or polisher, with a low cost price, which allows the cleaning and polishing of dental surfaces; which can be used by professionals as well as private individuals.

The instrument or polisher for cleaning the surface of the teeth is created in the shape of a rod and is characterized essentially by the structure of the rod which comprises fibers and optionally a load of particles embedded in a resinous matrix, the structure giving the working surface of the rod a continuous abrasive power effect and the rod being rigid.

In a first embodiment of this invention, the rod is made only of abrasive fibers embedded in a resinous matrix and is rigid.

In a second embodiment of this invention, the rod is made of abrasive fibers and a load of abrasive particles and is rigid, and the abrasive function created by the fibers or by the particles can be the same or different according to the choice of fibers and particles.

In a third embodiment: of this invention, the structure of the rod is created from non-abrasive fibers and abrasive particles embedded in a resinous matrix, the fibers only giving the rod solidity and the rod is rigid.

The structure of the rod can contain, in addition, a nucleus, made of a metal, a resin or a composite material, of a same or different type from the material forming the rod, and of the same or a different color.

The particles of the load allow, depending on their type, their shapes, their dimensions, and/or their quantity, to make varying the abrasive effect of the instrument, these particles, having preferably a hardness between 3 and 10 on the MOHS scale and a size between 2 and 25 microns, preferably between 14 and 25 microns, most preferably of 20 microns. The particles can be of the same size or have different sizes in order to diminish the interstitial spaces between adjacent particles and in order to promote regularity of the abrasive effect. The load of these particles can vary from 10 to 70% of the weight of the resin.

The particles of the load incorporated into the resin during the fabrication process, of the instrument or polisher i.e. by extrusion, coextrusion, or casting by compression, transfer-compression, injection or pultrusion, allow one to obtain the researched viscosity to promote the sliding of the resin during the polymerization in the dies or in the molds. The particles of the load can be made, according to the method of production of the invention's instrument or polisher to be obtained;

on one hand of materials with an abrasive power, such as calcium carbonate, calcined clad/, silica, glass or ceramic microspheres, aluminum oxide, such as alumina or even corindum, cerium oxide, tin oxide and mixtures or analogs thereof;

on the other hand of a material which does not possess an abrasive power but has a function of softening the abrasive effect procured by the fibers such as clay or hydrated kaolin, talc, or even Teflon® powder;

or a mixture of the two preceding material types.

According to the invention, the fibers can be continuous or not, parallel or not, or assembled, for example, in the shape of coils, braids, or links.

When hardened, the resinous matrix gives rigidity to the polisher of the invention.

Still according to the invention, the proportion of the volume of fibers will be preferably from 45 to 65% of the total volume of the fibers plus the resinous matrix and the fibers can be glass fibers and notably AR glass fibers. The most preferably the fibers are made of a glass which is enriched with zirconium oxide. They can also be quartz fibers, silica fibers, carbon fibers, or synthetic fibers, preferably aramide fibers such as Kevlar® fibers and will have a diameter of between 2 and 25 microns, preferably of between 14 and 25 microns and most preferably of 20 microns.

In the first preferred embodiment of the invention, the fibers are fibers made of a glass which is enriched with zirconium oxide. These fibers give the instrument or polisher a very good resistance to acidic and/or alkaline agents and make the instrument detectable by electromagnetic radiation and, notably by X-rays, i.e. by a mere and common medical radiography.

In the second preferred embodiment of the invention the fibers are fibers made of aramide, such as Kevlar®. These fibers enable to obtain a working surface, i.e. a polishing surface, of the instrument or polisher of the invention, with a felt texture. In this latter case, the aramide fibers do not have any polishing function but they have the function to give the polishing surface of the polisher of the invention a felt texture and also they act as a rigid skeleton in the polisher of the invention. Consequently, in this embodiment, it is necessary to add abrasive powders either in the resin matrix of the polisher of the invention or onto its polishing surface. Such preferred abrasive polishing powders are powders of inorganic materials such as tin oxide or cerium oxide or alumina and mixtures or analogs thereof.

The resinous matrix will be made of thermohardening polymer resins or thermoplastic polymer resins and, preferably, of epoxy or polyester resins and gives rigidity to the polisher of the invention.

The instrument or polisher of the invention can furthermore comprise surface treating agents, such as titanates, zirconates, or preferably silanes, in order to increase the adhesion of the particles to the resin.

The structure of the instrument or polisher according to the invention thus enables one to give the polisher the fineness required to access the tightest spaces between the teeth, without risk of fracture and without danger for the teeth or the periodontal area, as well as all the desired shapes to conform to the dental surfaces as-closely as possible.

In addition, the structure of the instrument or polisher according to the invention gives it a permanent abrasive power, because the abrasive agents are entirely a part of its structure and, as one goes along using this instrument, the working surface of the instrument or polisher always includes new sections of fibers and/or particles which insure its abrasive function.

Finally, its structure enables it to be cleaned, decontaminated, or sterilized and renders it an instrument or polisher perfectly adapted to the hygienic and biocompatibility requirements for a use in the oral cavity.

The instrument or polisher according to this -invention thus offers to private individuals a means of hygiene and maintenance of their teeth which is efficient, easy to use, without danger, and economical, also enabling them to eliminate the stains and undesirable discolorations, even in places difficult to access, and such a polisher had no equivalent until the invention.

The instrument or polisher of this invention enables dental professionals to gain a considerable time and efficiency and gives their patients, more comfort, and better results, without any loss of their dental integrity, and at a lower cost.

BRIEF DESCRIPTION OF THE DRAWINGS

The advantages and features of the present invention will become more clear in the following description, which is made in relation to the attached drawings representing a non-limiting embodiment.

DESCRIPTION OF THE PREFERRED EMBODIMENTS

Figure 1A:
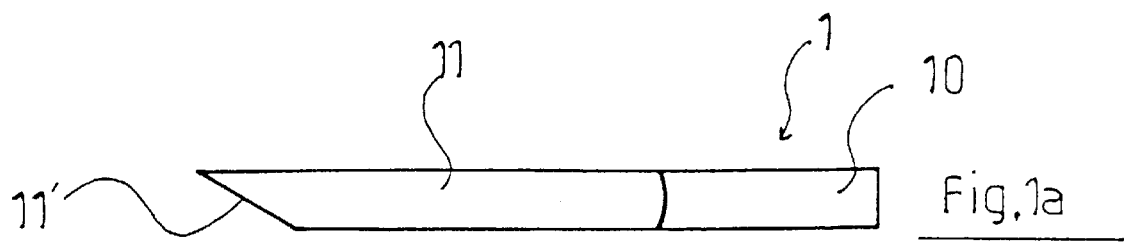
FIG. 1a is a profile view of a tooth-cleaning instrument or polisher according to the invention following a particular form.
Figure 1B:
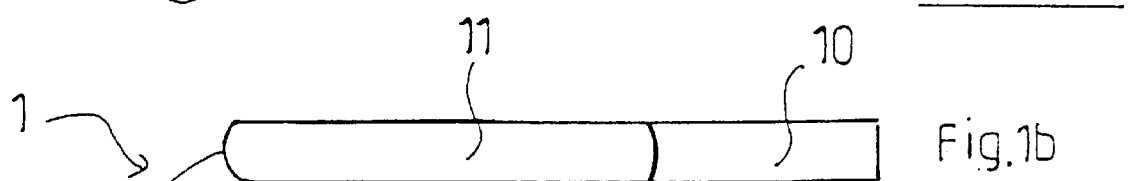
FIG. 1b is a profile view of a tooth-cleaning instrument or polisher according to the invention following another form.
Figure 1C:
FIG. 1c is a profile view of a tooth-cleaning instrument or polisher according to the invention according to another form.

If one refers to FIGS. 1a, 1b, and 1c, one can see that a tooth-cleaning instrument or polisher according to the present invention presents itself in the shape of a rod 1 consisting of a handle 10 to hold on to and a part 11 comprising a working end 11' enabling one to polish the surface of teeth. The handle 10 and part 11 will preferably be made of only one piece as is the case in the figures, or the handle 10 will be an added part.

Figure 1D:
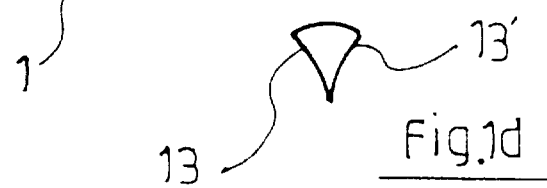
FIG. 1d is an end view of the instrument or polisher represented in FIG. 1c.

The part 11 has a cylindrical shape and its working end 11' is beveled obliquely (FIG. 1a), or in a manner more or less rounded (FIGS. 1b and 1c), or is straight. One can also see in FIGS. 1c and 1d that part 11 can also be beveled longitudinally in such a manner to form two adjacent sides 13, 13', forming a certain angle there between and slightly curved.

The working end 11' can have many diverse shapes in order to penetrate different spaces between teeth, especially very small spaces as well as, in order to be able to clean and polish the teeth by moving the rod in a back and forth, and up and down, movement in contact with the surfaces to be cleaned.

Figure 2:
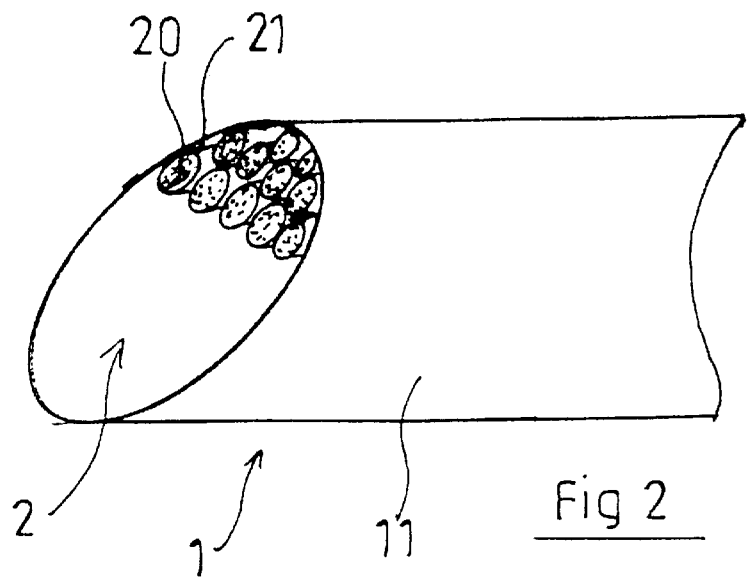
FIG. 2 represents a partial, transversely cut view of a tooth-cleaning instrument or polisher according to the invention in a preferred embodiment of its internal structure.

The polishing of the teeth is made possible thanks to the particular structure 2 of the rod 11 which gives it, during the entire polishing operation, an abrasive power which continuously renews itself. The structure 2 is made up of, as one can see on FIG. 2, abrasive fibers 20, each forming a file, embedded in a resinous matrix 21 preferably made on the basis of an epoxy resin.

In a particularly preferred embodiment, the instrument or polisher of the invention is constituted of fibers 20 made of glass enriched with zirconia $ZrO_2$, these fibers 20 being embedded in a resin matrix. The fibers 20 made of a glass which is enriched with zirconium oxide are fibers manufactured from a glass which has itself been manufactured by melting raw materials powders among which zirconium oxide or a precursor of zirconium oxide. In this glass, zirconium oxide replaces and substitutes to a part of the other usual constituents of a glass as well before as after the melting of the constituents of the glass i.e. the manufacture of the glass. For use in the invention the glass from which the fibers 20 are manufactured preferably contains between 15 and 20% by weight of zirconium oxide as compared to the total weight of the constituents of the glass and the most preferably between 16,8 and 17,1% by weight of zirconium oxide as compared to the total weight of the constituents of the glass. From this glass, glass fibers are spun and then embedded within a resin matrix. Then one gives :he desired shape to the instrument or polisher of the invention and, as already described, the working end 11' is beveled either obliquely or in a more or less rounded fashion or longitudinally in order to form two adjacent faces 13, 13', which make a certain angle between them and slightly curved.

This polisher containing fibers of a glass enriched with zirconium oxide possesses numerous advantages.

First of all, the fibers 20 made of a glass enriched with zirconium oxide are resistant to acid and/or alkaline agents and consequently render the polishes- of the invention resistant to acid and/or alkaline agents. This is very interesting because the mouth is a medium which can alternatively be acid or alkaline.

That is to say that the fibers 20 made of a glass enriched with zirconium oxide, contrarily to classic glass fibers made of glass non enriched with zirconium oxide, are not attacked by acid or alkaline agents present in the mouth, during their use in the mouth, and consequently do not lead to the formation of residues which could be noxious.

Furthermore, the fibers 20 made of a glass enriched with zirconium oxide are radiopaque to electromagnetic radiations and thus render the instrument or polisher of the invention detectable by X-rays, enabling to locate it in case of accidental ingestion.

But more importantly, contrarily to the classic glass fibers which form small fibrils when used as a polisher, these fibrils overrunning the mouth, the fibers made of a glass which is enriched with zirconium oxide do not produce such fibrils.

Indeed, a dental instrument or polisher made from fibers of classic glass, i.e. non enriched with zirconium oxide, when used as a polisher, forms small fibrils which are irritating and even dangerous for the mucosa and soft parts of the user. These fibrils are even more dangerous if they are swallowed. The user, when using a polisher constituted of such fibers made of a classic glass, such as AR glass, has the mouth filled with such fibrils, rendering such a polisher particularly dangerous and unpleasant to use. In contrast, the polisher of the invention made from fibers of a glass enriched with zirconium oxide does not have such drawbacks.

In a second particularly preferred embodiment of the invention, the instrument or polisher of the invention is constituted of aramide fibers, such as Kevlar® fibers, embedded in a resin matrix. The aramide fibers are particularly advantageous because when they are put at the desired shape, for example by machining, they produce filaments which do not completely take off from the machined part. This behavior is generally considered as a drawback of these fibers but, in the case of the polisher of the invention, this behavior is an advantage.

Indeed, during the manufacture of the beveled working end 11' of the polisher of the invention, this behavior enables to create a surface of the working end 11' which has a felted texture, and this is particularly advantageous in the case of a polisher.

However, the aramide fibers do not have any polishing function. Here, they have the function to create the rigid skeleton of the polisher of the invention and also to create a surface of the working end 11' having a felted texture. Then it is necessary to add abrasive powders in the resin matrix of the polisher of the invention. However the abrasive powders may also be added onto the surface of the working end 11', before each use. Preferred abrasive powders which can be used for this aim are powders of tin oxide or cerium oxide or alumina and a mixture thereof.

Whereas the polisher according to the first preferred embodiment of the invention in which the fibers 20 are fibers made of a glass which is enriched with zirconium oxide is more particularly designed for a domestic use, by the private individual, the polisher of the invention according to the second preferred embodiment in which the fibers 20 are aramide fibers and in which the resin matrix furthermore contains abrasive agents such as tin oxide, cerium oxide or alumina, is more particularly designed for a use by a professional. Indeed, it can be used not only by hand, but also fixed to an ap oaratus capable to put it in rotation or vibration.

In any cases, the proportion of the fibers 20 is advantageously between 45 and 65% by volume of the total volume of the fibers plus the resinous matrix, in order to obtain a good polishing power, and the fibers 20 preferably have a diameter of between 2 and 25 microns, preferably of between 14 and 25 microns, and most preferably of 20 microns.

The fibers 20 are preferably continuous fibers embedded in a resin matrix which do not produce particles that can disseminate into the oral cavity.

Another common advantage of the polishers according to the first and second preferred embodiments of the invention is that they are usable not only for polishing natural teeth but also composite materials which are used as dental filling material or as material for a dental prosthetic element.

In particular, the polisher, according to the first preferred embodiment of the invention in which the fibers 20 are fibers made of a glass which is enriched with zirconium oxide, can be used for giving the shape to the composite material and for obtaining a smooth and appropriate surface of the dental composite material. However, the dental composite material after such a polishing with such a polisher, has a matte finish and therefore should be rendered bright by a finer polishing. This is advantageously obtained by using the polisher according to the second preferred embodiment of the invention in which the fibers 20 are aramide fibers, this polisher being preferably placed on a device which enables to put the polisher of the invention in rotation or vibration. This finishing enables to attain a bright aspect which is very closed from, if not identical to, the natural dental enamel.

It is to be noted that when the polisher according to the first preferred embodiment of the invention in which the fibers 20 are fibers made of a glass which is enriched with zirconium oxide is used on natural tooth. It does not abrade the enamel so that the natural tooth keeps its bright aspect.

Thus, the instrument or polisher of this invention allows cleaning and polishing of the dental tissue, while respecting the tooth as well as cleaning and polishing parts made of a composite material for dental restoration, and because of its bio-compatible characteristics, is particularly adapted to the required conditions for use in the oral cavity.

Finally, its abrasive power can be chosen and determined according to the needs by acting on the nature of each of these constituents, that is to say, the fibers and/or the particles embedded in the resin matrix.

The abrasive action is given by the working end 11' of the fibers 20, this abrasive action consequently renewing itself as one goes along using the instrument or polisher of the invention.

As already stated, in all the embodiments of the invention, the polisher is rigid due to the hardened resinous matrix.

The polisher of the invention is most preferably manufactured by the pultrusion process which means that the fibers are essentially continuous fibers extending along the axial direction of the polisher.

What is claimed is:

1. Hygiene instrument for the cleaning and polishing of the surface of teeth and/or the composite materials of dental fillings, said instrument having the shape of a rod, the structure of which comprises fibers embedded in a resinous matrix wherein the fibers are made from a glass enriched with zirconium oxide, giving to the instrument a high resistance to at least one of an alkaline and acidic agent and making the instrument detectable by electromagnetic radiation.

2. The instrument according to claim 1 wherein said glass enriched with zirconium oxide contains between 15 and 20 wt % of zirconium oxide as compared to the total weight of the glass.

3. The instrument according to claim 1 wherein said glass enriched with zirconium oxide contains between 7.1 aid 7.8 wt % of zirconium oxide as compared to the total weight of the glass.

4. The instrument according to claim 1 wherein the structure of the rod furthermore comprises aramide fibers.

5. The instrument according to claim 1 wherein the structure of the rod furthermore comprises a load of particles.

6. The instrument according to claim 1 wherein the structure of the rod furthermore includes a nucleus made of one of a metallic material, a resin, and a composite material.

7. The instrument according to claim 1 wherein the resin matrix is made of one of a thermohardening polymer matrix and a thermoplastic polymer matrix.

8. The instrument according to claim 1 wherein the rod has cylindrical shape and has one end which is beveled.

9. The instrument according to claim 8 wherein the beveled end is longitudinally beveled in such a manner to form two adjacent sides making a specific angle therebetween.

10. The instrument according to claim 1 comprising a handle formed as one piece with the rod.

11. Hygiene instrument for the cleaning and polishing of the surface of the teeth and/or the composite materials of dental fillings, said instrument having the shape of a rod, the structure of which comprises fibers embedded in a resinous matrix wherein the rod comprises aramide fibers and particles of abrasive powders embedded in an epoxy resin matrix.

* * * * *